United States Patent [19]

Smith et al.

[11] 4,010,209

[45] Mar. 1, 1977

[54] PROCESS

[75] Inventors: Curtis P. Smith, Cheshire; Henri Ulrich, Northford, both of Conn.

[73] Assignee: The Upjohn Company, Kalamazoo, Mich.

[22] Filed: Dec. 15, 1975

[21] Appl. No.: 640,716

[52] U.S. Cl. .................. 260/606.5 P; 260/307 R; 260/340.7; 260/345.9; 260/347.8

[51] Int. Cl.$^2$ .......................................... C07F 9/53

[58] Field of Search ......... 260/606.5 P, 307, 340.7, 260/345.9, 347.8

[56] References Cited

UNITED STATES PATENTS

| | | | |
|---|---|---|---|
| 2,663,737 | 12/1953 | McCormack | 260/606.5 P |
| 2,663,738 | 12/1953 | McCormack | 260/606.5 P |
| 2,663,739 | 12/1953 | McCormack | 260/606.5 P |
| 2,853,473 | 9/1958 | Campbell et al. | 260/606.5 P X |
| 2,853,518 | 9/1958 | Balon | 260/606.5 P X |
| 3,139,449 | 6/1964 | Ahramjian | 260/606.5 P X |
| 3,331,878 | 7/1967 | Priestley | 260/606.5 P |
| 3,345,287 | 10/1967 | Voetter et al. | 260/681.5 R X |

OTHER PUBLICATIONS

Vizel J. Gen. Chem. (USSR), V43, No. 10, pp. 2137–2143 (1973).

*Primary Examiner*—Helen M. S. Sneed
*Attorney, Agent, or Firm*—Denis A. Firth; John Kekich

[57] ABSTRACT

A process is described for the preparation of phospholene-1-oxides and 1-sulfides having an aliphatic substituent in the 1-position, a double bond at the 2- or 3-positions and, optionally, having additional substituents at one or more of positions 2, 3, 4 or 5. The process comprises the reaction of a 1-(2-chloroalkoxy)-phospholene with the appropriate aliphatic alcohol or thiol optionally in the presence of an alkylation catalyst. Use of an aliphatic alcohol gives rise to a phospholene oxide while use of the corresponding thiol gives rise to a phospholene sulfide. The phospholene-1-oxides and 1-sulfides so obtained are useful as catalysts for the conversion of isocyanates to carbodiimides.

13 Claims, No Drawings

PROCESS

BACKGROUND OF THE INVENTION

1. Field of the Invention

This invention relates to a novel process for the preparation of heterocyclic phosphorus compounds and is more particularly concerned with the preparation of 1-aliphatically substituted-2 or 3-phospholene-1-oxides and 1-sulfides.

2. Description of the Prior Art

U.S. Pat. No. 2,663,737 describes the preparation of 1-hydrocarbyl-substituted phospholene oxides by condensing butadiene, or a substituted butadiene, with the appropriate dihalohydrocarbylphosphine and hydrolyzing the intermediate 1,1-dihalo-1-hydrocarbylphospholene by adding water to the reaction product.

U.S. Pat. No. 2,663,738 describes the preparation of the corresponding 1-hydrocarbyl-substituted phospholene sulfides by an analogous method.

U.S. Pat. No. 2,853,473 describes the use of the 1-hydrocarbyl-substituted phospholene 1-oxides and 1-sulfides so obtained as catalysts for the conversion of isocyanates to carbodiimides.

Vizel et al., J. Gen. Chem. (USSR), 43, No. 10, 2137 – 2143, 1973, show an Arbuzov reaction in which a 1-hydrocarbyloxyphospholene is reacted with an alkyl halide and the alkyl of the latter is shown as becoming attached to phosphorus. In our experience no such reaction takes place.

Commercial demand for the above phospholene derivatives has recently increased due to the usefulness of these compounds in the preparation of polymeric foams containing carbodiimide linkages, which latter foams are finding increasing use as insulating materials characterized by thermal stability, low flame spread ratings and low levels of smoke generated under fire conditions.

It is an object of this invention to provide improved methods for the preparation of the above phospholene derivatives. In particular, it is an object of this invention to provide methods which reduce significantly the cost of production of the above phospholene derivatives. Since the cost of the phospholene derivatives is a relatively large proportion of the total cost of preparing polymeric foams containing carbodiimide linkages, such a reduction in manufacturing costs for the phospholene derivatives necessarily gives rise to a corresponding reduction in the cost of preparing the polymer foams.

Other advantages in the development of the novel process of the invention will become apparent from the description which follows.

SUMMARY OF THE INVENTION

This invention comprises a process for the preparation of a phospholene-1-oxide or 1-sulfide having an aliphatic hydrocarbyl substituent in the 1-position which process comprises reacting the appropriate 1-(2-chloroalkoxy)-phospholene with the appropriate aliphatic alcohol or thiol at a temperature within the range of about −20° to 160° C.

In a particular embodiment of the process of the invention the above reaction is carried out in the presence of a catalytic amount of an alkylating agent such as an alkyl bromide or alkyl iodide.

The system of nomenclature employed throughout this specification and the claims which follow is that conventionally used in the art. Illustratively, a 1-alkyl-3-phospholene-1-oxide is represented by the formula (I) and a 1,3-dialkyl-2-phospholene-1-oxide is represented by the formula (II):

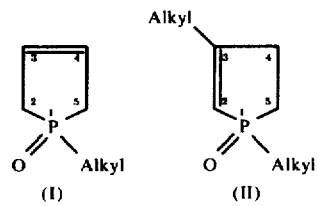

The term "aliphatic hydrocarbyl" means the radical obtained by removing a hydrogen atom from an aliphatic hydrocarbon, preferably one having up to 12 carbon atoms inclusive. Illustrative of aliphatic hydrocarbyl are: alkyl from 1 to 12 carbon atoms, inclusive, such as methyl, ethyl, propyl, butyl, pentyl, hexyl heptyl, octyl, nonyl, decyl, undecyl, dodecyl and isomeric forms thereof; alkenyl from 3 to 12 carbon atoms, inclusive, such as propenyl, butenyl, pentenyl, hexenyl, heptenyl, octenyl, nonenyl, decenyl, undecenyl, dodecenyl and isomeric forms thereof; alkynyl from 3 to 12 carbon atoms, inclusive, such as propynyl, butynyl, pentynyl, hexynyl, heptynyl, octynyl, nonynyl, decynyl, undecynyl, dodecynyl and isomeric forms thereof; and cycloalkyl from 4 to 12 carbon atoms, inclusive, such as cyclobutyl, cyclopentyl, cyclohexyl, cycloheptyl, cyclooctyl, dimethylcyclohexyl, hexylcyclohexyl, and isomeric forms thereof.

DETAILED DESCRIPTION OF THE INVENTION

The process of the invention can be applied to the conversion to the corresponding phospholene-1-oxide or phospholene-1-sulfide of any 1-(2-chloroalkoxy)-phospholene (III) which has a double bond between the 2 and 3 carbon atoms, or between the 3 and 4 carbon atoms, and which optionally has inert substituents on one or more of the carbon atoms 2, 3, 4 or 5 of the heterocyclic phosphorus ring. By inert substituent is meant any substituent which is inert under the conditions of the reaction, i.e does not enter into reaction with any of the other reactants employed in the process or interfere in any other way with the desired progress of the reaction. Illustrative of inert substituents are halogen, i.e. fluorine, chlorine, bromine, iodine; loweralkoxy such as methoxy, ethoxy, propoxy, butoxy, pentoxy, hexyloxy and isomeric forms thereof; phenoxy; hydrocarbyl from 1 to 6 carbon atoms, inclusive, and halo-substituted hydrocarbyl from 1 to 6 carbon atoms, inclusive.

The term "hydrocarbyl from 1 to 6 carbon atoms" means the monovalent radical obtained by removing one hydrogen atom from a parent hydrocarbon of the stated carbon content. Illustrative of such hydrocarbyl groups are alkyl such as methyl, ethyl, propyl, butyl, pentyl, hexyl and isomeric forms thereof; alkenyl such as vinyl, allyl, butenyl, pentenyl, hexenyl and isomeric forms thereof; cycloalkyl such as cyclobutyl, cyclopentyl and cyclohexyl; and phenyl.

The term "halo-substituted hydrocarbyl from 1 to 6 carbon atoms" means hydrocarbyl as above defined wherein one or more of the hydrogen atoms in said hydrocarbyl has been replaced by halogen. Illustrative of halo-substituted hydrocarbyl are chloromethyl, trichloromethyl, trifluoromethyl, 2-chloroethyl, 2,3-dichlorobutyl, 2-chlorobutenyl, 2-bromohexyl, 4-chlorophenyl, 3-fluorophenyl, 2-chloropropenyl, and the like.

In carrying out the process of the invention the 1-(2-chloroalkoxy)-phospholene (III) is reacted with the appropriate aliphatic alcohol or thiol (IV). The proportions of the two reactants are advantageously substantially stoichiometric, i.e. there is substantially one equivalent of the alcohol or thiol (IV) for each mole of the phospholene (III). However, an excess of the alcohol or thiol (IV) can be employed if desired. The reaction is conveniently carried out at elevated temperatures of the order of about 50° to 140° C although, in the case of certain alcohols such as the acetylenic alcohols, the reaction is highly exothermic and the reaction mixture requires cooling to temperatures of the order of −30° C or less in order to control the reaction effectively.

If desired the reaction is carried out in the presence of an inert solvent such as benzene, xylenes, methylene chloride, 1,2-dichloroethane, and the like. However, in a preferred embodiment of the invention the alcohol or thiol (IV) is employed in excess of the stoichiometric amount and thereby serves as solvent for the reaction without the need to employ an inert solvent.

The order in which the phospholene (III) and the alcohol or thiol (IV) are brought together is not critical but it is generally more convenient to add the alcohol or thiol (IV) to the phospholene (III), rather than vice versa, with appropriate cooling and stirring in those cases mentioned above in which the reaction is exothermic.

The progress of the reaction can be followed by routine analytical procedures, such as infrared spectroscopic analysis of an aliquot. Once the reaction is thereby determined to be complete, the desired phospholene-1-oxide or 1-sulfide is isolated from the reaction product by routine procedures, for example, by distillation to remove any excess alcohol or thiol (IV) and any by-products generated in the reaction, followed by purification of the residue, if desired, by distillation, fractional crystallization (in the case of solids) and the like. In many cases, as will be discussed in more detail below, it has been found that the crude reaction product, after treatment to remove excess alcohol or thiol (IV) and the like, can be used satisfactorily without purification, as a carbodiimide forming catalyst in the preparation of polycarbodiimides particularly polycarbodiimide foams.

In a particular embodiment of the process of the invention, the phospholene (III) and the alcohol or thiol (IV) are brought together in the presence of a catalytic amount of an alkylating agent. Alkyl halides, preferably alkyl bromides and alkyl iodides, wherein alkyl contains from 1 to 12 carbon atoms as hereinbefore exemplified, are employed as alkylating agents. A particularly preferred alkylating agent is ethyl bromide. By "catalytic amount" is meant a proportion of alkylating agent within the range of about 0.05 mole to 0.5 mole per mole of phospholene (III) and preferably an amount within the range of about 0.1 mole to 0.2 mole per mole of phospholene (III).

The alcohols and thiols (IV) which are employed in the process of the invention can be any aliphatic mono- or polyhydric alcohol or thiol, advantageously one having a carbon atom content of up to 12 carbon atoms. Illustrative of the alcohols (IV) are alkanols such as methanol, ethanol, propanol, butanol, pentanol, hexanol, heptanol, octanol, nonanol, decanol, undecanol, dodecanol and isomeric forms thereof; alkenols such as propenol, butenol, pentenol, hexenol, heptenol, octenol, nonenol, decenol, undecenol, dodecenol and isomeric forms thereof; alkynols such as ethynol, propynol, butynol, pentynol, hexynol, heptynol, octynol, nonynol, decynol, undecynol, dodecynol, and the like; cycloaliphatic alcohols such as cyclopentanol, cyclohexanol, cycloheptanol, cyclooctanol, methylcyclohexanol, dimethylcyclohexanol, cyclohexylcyclohexanol, and isomeric forms thereof; cyclopentenol, cyclohexenol, dimethylcyclohexenol and the like; aliphatic heterocyclic alcohols such as 2,2-dimethyl-4-hydroxymethyl-1,3-dioxolane, N-(2-hydroxyethyl)oxazolidine, 5-hydroxy-1,3-dioxane, furfuryl alcohol, and the like; polyhydric alcohols such as glycerol, hexane-1,2-diol, pentaerythritol, propylene glycol, ethylene glycol, dipropylene glycol, polyethylene glycols and polypropylene glycols having molecular weights up to 1000; fructose, glucose, ribose, arabinose and like sugars.

Illustrative of the aliphatic thiols (IV) which can be employed in the process of the invention are alkyl mercaptans such as methyl, ethyl, propyl, butyl, pentyl, hexyl, heptyl, octyl, nonyl, decyl, undecyl and dodecyl mercaptans including isomeric forms thereof; alkenyl mercaptans such as allyl, butenyl, pentenyl, hexenyl, heptenyl, octenyl, nonenyl, decenyl, undecenyl, and dodecenyl mercaptan including isomeric forms thereof; alkynyl mercaptans such as propynyl, butynyl, pentynyl, hexynyl, heptynyl, octynyl, nonynyl, decynyl, undecynyl, and dodecynyl mercaptan including isomeric forms thereof; cycloalkyl mercaptans such as cyclobutyl, cyclopentyl, cyclohexyl, cycloheptyl, and cyclooctyl mercaptans; cycloalkenyl mercaptans such as cyclopentenyl, cyclohexenyl, cycloheptenyl and cyclooctenyl mercaptans; and aliphatic polythiol compounds such as 1,2-dimercaptobutane, 1,2-dimercaptohexane, and the like.

It is believed that the reaction which takes place in accordance with the process of the invention involves a transesterification as the first step, the ester interchange involving replacement of the 1-(2-chloroalkoxy)-group in the starting phospholene (III) by the aliphatic hydrocarbyloxy or aliphatic hydrocarbylthio residue of the alcohol or thiol (IV). The transesterification step is believed to be followed immediately by a rearrangement in which the aliphatic hydrocarbyl residue becomes attached directly (i.e. by a C-P bond) to the phosphorus atom of the phospholene. The above sequence of reactions is illustrated by the following example in which 1,3-dimethyl-2-phospholene-1-oxide is prepared by reaction of 3-methyl-1-(2-chloropropoxy)-2-phospholene with methanol.

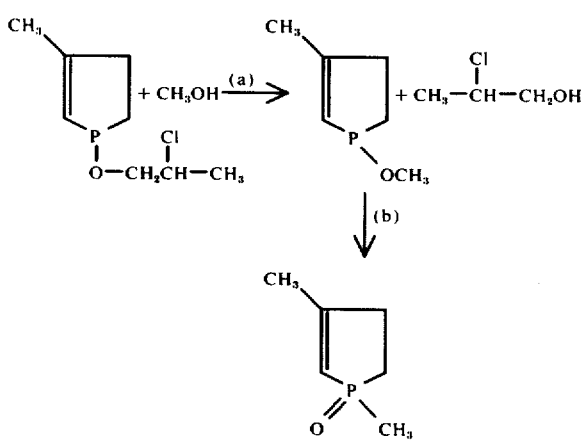

Step (a) represents the transesterification step and Step (b) represents the rearrangement step in the above reaction.

Similarly the following example represents the reactions believed to occur when the process of the invention is applied to the reaction of 3-methyl-1-(2-chloropropoxy)-2-phospholene with methyl mercaptan to produce 1,3-dimethyl-2phospholene-1-sulfide:

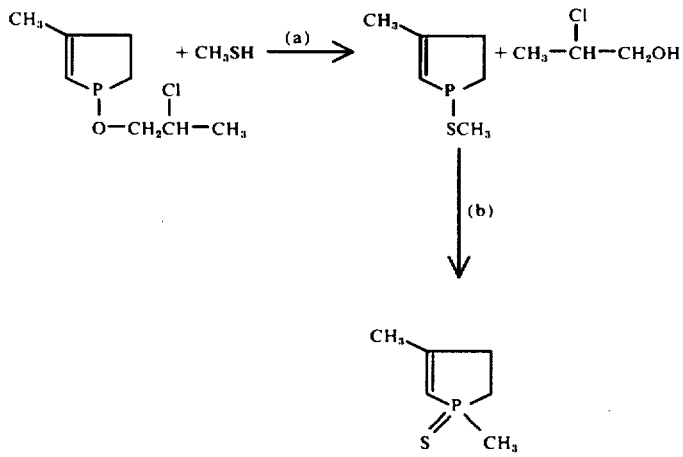

It is to be understood that the above reaction mechanism is offered only for purposes of promoting a better understanding of the process of the invention and is not to be construed as limiting the scope of the present invention or disclosure. Thus, whatever the mechanism involved, the overall result of the process of the invention is that set forth above. In particular it is to be noted that the product of the reaction with an alcohol will be a phospholene-1-oxide and the product of the reaction with a thiol will be a phospholene-1-sulfide.

It has been found, in general, that when the starting phospholene (III) has the double bond between carbon atoms 2 and 3, i.e. in the 2-position, the phospholene-1-oxide or phospholene-1-sulfide obtained in the process of the reaction has the double bond in the same position. However, when the starting phospholene (III) has the double bond between carbon atoms 3 and 4, i.e. in the 3-position, the phospholene-1-oxide or phospholene-1-sulfide obtained in the process of the reaction is generally a mixture of the two possible isomers having the double bond in either the 2 or 3 position. The proportion of the two isomers in such mixtures is found to vary depending upon the particular phospholene starting material.

Further, it has been found that, when the phospholene starting material (III) has the double bond in the 3-position, the formation of the isomer of the end product having the double bond in the 2-position can be suppressed, either partially or wholly, by employing an alkylating agent, as hereinbefore defined, in the process of the invention. The higher the molar proportion of alkylating agent employed, the lower the amount of the 2-isomer produced. In general, the use of amounts of alkylating agent in the proportion of 0.3 mole, or higher, per mole of phospholene starting material (III) will substantially eliminate the formation of 2-isomer in the product. The proportion of alkylating agent necessary to employ in any given instance to achieve this result can readily be determined by a process of trial and error.

When the alcohol or thiol (IV) employed in the reaction is a polyhydric alcohol or thiol, i.e. contains 2 or more hydroxy and or thiol groups, the process of the invention gives rise to a phospholene-1-oxide or phospholene-1-sulfide in which the aliphatic radical attached to phosphorus contains 1 or more free hydroxy or thiol groups (i.e. one such group less than the number present in the starting alcohol or thiol). Such compounds are useful for chemical incorporation into polymers, particularly polyisocyanurates and polyurethanes which are based on polyisocyanates, and which impart flame retardancy to the resulting polymers.

In a particular application of the process of the invention it is possible to employ as the aliphatic alcohol a material such as cellulose which has a plurality of hydroxyl groups attached to aliphatic carbon atoms. By such a process there is obtained a cellulosic material to which is chemically bonded, by C-P bonds, a plurality of phospholene moieties, which moieties impart flame retardant properties to the cellulosic material. Accordingly, the process of the invention, in this particular embodiment, offers means for imparting flame retardancy to garments and other articles such as sheets, draperies and the like, made from cotton and like cellulosic materials.

The phospholenes (III) employed as starting materials in the process of the present invention are for the most part well-known in the art. For example, a wide variety of such materials is described in our issued U.S.

Pat. No. 3,767,708. A representative group of compounds which can be employed as starting materials in the process of the invention is that shown by the following formula:

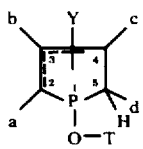

wherein a, b, c and d are each selected from the group consisting of hydrogen, halogen, alkoxy from 1 to 6 carbon atoms, inclusive, phenoxy, hydrocarbyl from 1 to 6 carbon atoms, inclusive (as hereinbefore defined), and halo-substituted hydrocarbyl from 1 to 6 carbon atoms, inclusive (as hereinbefore defined); the broken lines indicate that a double bond is located between the carbon atom at position 3 and one of the two carbon atoms at positions 2 and 4; Y represents hydrogen attached to whichever carbon atom at positions 2 and 4 is not part of the double bond; and T is 2-chloroalkyl wherein alkyl has from 2 to 6 carbon atoms. Particularly useful as starting materials in the process of the invention are those compounds of the formula in which the group —O—T represents chloroethoxy or 2-chloropropoxy.

The compounds of the above formula are obtained by reaction of the appropriate 1-chlorophospholene with the appropriate alkylene oxide as described in the aforesaid U.S. Pat. No. 3,767,708.

Further, it is generally not necessary to isolate and/or purify the intermediate 1-(2-chloroalkoxy) compounds obtained by latter reaction before submitting them to the process of the invention. For example, a 1-chlorophospholene can be reacted with ethylene or propylene oxide and the reaction product can be reacted, without isolation, with the appropriate alcohol or thiol in accordance with the process of the invention.

The process of the invention provides a highly convenient method which is of general applicability to the preparation of phospholene-1-oxides and 1-sulfides. The ease of operation and the high overall yields achieved by the process are in marked contrast to the results achieved in the known direct reaction of 1-chlorophospholenes with alcohols or thiols. One of the major difficulties encountered in the latter process lies in the need to employ pyridine or like tertiary amines as scavengers for the hydrogen chloride eliminated in the reaction. The voluminous precipitate of amine hydrochloride produced thereby has to be separated from the reaction product by filtration leading to cumbersome procedures in commercial production. In addition, the known process is of much more limited applicability than that described herein.

As set forth above, the phospholene-1-oxides and 1-sulfides which are produced in accordance with the process of the invention are known to be useful as catalysts for the conversion of isocyanates to carbodiimides. We have now found, surprisingly, that the reaction products obtained in the process of the invention can be used as catalysts for such reactions directly, if desired, without any purification other than removal of volatile impurities. Further, in certain instances, the catalytic activity of the crude products (by crude is meant a product obtained in the process of the invention which has been separated from volatile impurities but which has not been subjected to other purification procedures such as distillation, recrystallization, and the like) is significantly greater than would be expected based on the content of phospholene-1-oxide or sulfide therein. This finding is of importance from an economic standpoint insofar as the use of crude material, as opposed to the more expensive pure material, substantially reduces the overall cost of preparing carbodiimides. This is a significant finding since the material cost of the catalyst is a major part of the overall cost of preparing the carbodiimide even though the proportion of catalyst employed in the reaction is very minor.

The following examples describe the manner and process of making and using the invention and set forth the best mode contemplated by the inventors of carrying out the invention but are not to be construed as limiting.

EXAMPLE 1

Preparation of 1,3-dimethylphospholene-1-oxide

A mixture of 2 g. (0.0112 mole) of 1-(2-chloroethoxy)-3-methyl-3-phospholene (U.S. Pat. No. 3,767,708, Example 5), 5 ml. (0.065 mole) of ethyl bromide and 4 ml. of anhydrous methanol (previously dried over molecular sieves) was heated under reflux for 1.5 hour. At the end of this time examination of an aliquot by nuclear magnetic resonance spectroscopy showed no significant amount of absorption due to trivalent phosphorus. The ethyl bromide and methanol were evaporated and the residue was distilled in vacuo to obtain 1.1 g. (75% theoretical yield) of 1,3-dimethyl-3-phospholene-1-oxide in the form of a liquid having a boiling point of 84° to 91° C at 0.5 mm.

It is to be noted that, if the reaction reported by Vizel et al., supra, between a 1-hydrocarboxyphospholene and an alkyl halide were to proceed as they describe, the above reaction would have resulted in 1-ethyl-3-methyl-3-phospholene-1-oxide whereas no trace of this product was found even though a considerable excess (on a molar basis) of ethyl bromide was employed.

EXAMPLE 2

Preparation of 1-ethyl-3-methyl-3-phospholene-1-oxide

A mixture of 1.8 g. (0.010 mole) of 1-(2-chloroethoxy)-3-methyl-3-phospholene, 5 ml. of chloroform and 2 ml. of absolute ethanol was treated with 2 ml. (0.026 mole) of ethyl bromide. The mixture was allowed to stand at room temperature (circa 20° C) for approximately 3 hours and was then heated under reflux for 1 hour. At the end of that time the solvents and ethyl bromide were evaporated and the residue was distilled under reduced pressure to obtain 0.8 g. (55.6% theoretical yield) of 1-ethyl-3-methyl-3-phospholene-1-oxide in the form of a liquid having a boiling point of 90° – 105° C at 0.3 mm. of mercury.

EXAMPLE 3

Preparation of 1-allenyl-3-methyl-3-phospholene-1-oxide

To a solution of 2 g. (0.0112 mole) of 1-(2-chloroethoxy)-3-methyl-3-phospholene in 5 ml. of chloroform was added, slowly with agitation and cooling, a total of 2 ml. (0.034 mole) of prop-1-yn-3-ol over a period of 1 minute. The reaction was exothermic. The resulting yellow solution, after the initial exotherm had ceased, was heated under reflux for 15 minutes. Thereafter the solvent and excess propynol were removed by distillation and the residue was distilled in vacuo to obtain 0.9 g. (52% theoretical yield) of 1-allenyl-3-methyl-3-phospholene-1-oxide in the form of a liquid having a boiling point of 106° C at 0.3 mm. of mercury. It was found by nuclear magnetic resonance and infrared spectroscopy that the above product contained a minor proportion of the corresponding 1-propynyl isomer but the major product was the 1-allenyl isomer derived by isomerization of the propynyl group during the reaction.

EXAMPLE 4

Conversion of 1-chloro-3-methyl-3-phospholene to 1,3-dimethyl-3-phospholene-1-oxide without isolation of intermediates To a solution of 128.6 g. (0.956 mole) of 1-chloro-3-methyl-3-phospholene in 400 ml. of 1,2-dichloroethane was added, with stirring at 5° to 10° C. over a period of 15 minutes, a total of 66.7 g. (1.15 mole) of ethylene oxide. The resulting solution was maintained at 15° C with stirring for 30 minutes whereupon 91.8 g. (2.868 mole) of anhydrous methanol was added. The mixture was stirred for 15 minutes and then 10.4 g. (0.1 mole) of ethyl bromide was added. The resulting mixture was stirred at room temperature for 1 hour and then heated gradually to reflux and maintained thereat for 2 hours. During the period of heating prior to reflux a second quantity (10.4 g.) of ethyl bromide was added. The final product, after refluxing, was a yellow solution which was then evaporated to remove solvent, the last traces being removed in vacuo. The residue was distilled in vacuo to obtain 123.6 g. (96% theory) of 1,3-dimethylphospholene-1-oxide having a boiling point of 84° C at 0.6 mm. of mercury. The product was shown to contain approximately equal amounts of the 2- and 3-isomers.

EXAMPLE 5

Conversion of 1-chloro-3-methyl-3-phospholene to 1,3-dimethylphospholene-1-oxide without isolation of intermediates in the presence of different proportions of alkylating agent To a solution of 39.4 g. (0.293 mole) of 1-chloro-3-methyl-3-phospholene in 122.6 ml. of 1,2-dichloroethane was added slowly, with stirring, over a period of 10 minutes, a total of 20.45 g. (0.352 mole) of propylene oxide. The temperature of the reaction mixture was maintained at 5° to 10° C throughout the addition. The resulting mixture was stirred for 30 minutes at room temperature (circa 20° C) before adding 35.5 ml. of anhydrous methanol and stirring the mixture for a further 15 minutes. An aliquot (50 ml.) of the resulting solution was removed and added to 20 ml. (0.27 mole) of ethyl bromide and the mixture so obtained was heated under reflux for 1 hour. To the remainder of the above solution was added 2 ml. (0.027 mole) of ethyl bromide and the mixture was stirred for 1 hour at room temperature. Examination of an aliquot by nmr showed some trivalent phosphorus still present. Accordingly, a further 1.5 ml. (0.02 mole) of ethyl bromide was added and the mixture was heated under reflux for 1.5 hr.

The above reaction products were worked up separately by evaporating the solvents and ethyl bromide. The residues were examined by nmr. It was found that the product derived using the large excess of ethyl bromide was exclusively 1,3-dimethyl-3-phospholene-1-oxide whereas the product obtained using the much smaller proportion of ethyl bromide was a mixture of the 2- and 3-isomers in the relative proportions of 0.86:1.

EXAMPLE 6

Preparation of 1-(2-hydroxyethyl)-3-methylphospholene-1-oxide

To a solution of 14.7 g. (0.076 mole) of 1-(chloropropoxy)-3-methyl-3-phospholene in 50 ml. of 1,2-dichloroethane was added, with stirring, over a period of 5 minutes, a total of 14.14 g. (0.23 mole) of ethylene glycol. The resulting solution was cloudy. Ethyl bromide (1.66 g.) was added and the mixture was heated under reflux for 1 hour. At the end of this time the solvent and other volatile materials were removed by evaporation and the residue was distilled under reduced pressure. There was thus obtained 1.3 g. (10.6% theoretical yield) of a mixture of the 2- and 3-isomers of 1-(2-hydroxyethyl)-3-methylphospholene-1-oxide in the form of a liquid having a boiling point of 125° – 150° C at 0.2 mm. of mercury. A glassy residue remained in the distillation flask and was believed to be 1,1'-ethylenebis-(3-methylphospholene-1-oxide).

EXAMPLE 7

Preparation of 1-allenyl- and 1-propynyl-3-methyl-3-phospholene-1-oxide.

A solution of 10.6 g. (0.055 mole) of 1-(chloropropoxy)-3-methyl-3-phospholene in 25 ml. of methylene chloride was cooled to 0° C and maintained thereat while a total of 3.08 g. (0.055 mol.) of prop-1-yn-3-ol in 10 ml. of methylene chloride was added over a period of 20 minutes with stirring. The resulting mixture was stirred for a further 2 hours with cooling in an ice bath and then overnight at room temperature (circa 20° C). The solvent was stripped from the resulting mixture and the residue was distilled to give 5.3 g. of a mixture of approximately equal parts of 1-allenyl- and 1-propynyl-3-methyl-3-phospholene-1-oxide having a boiling point of 104° to 112° C at 0.2 mm. of mercury.

An aliquot (5 g.) of the above mixture was dissolved in 25 ml. of anhydrous methanol containing 0.1 g. of sodium methoxide and the mixture was allowed to stand overnight at room temperature (circa 20° C) before being heated under reflux for 7.5 hours. At the end of this time the solvent was evaporated and the residue was distilled in vacuo to give a total of 4.6 g. of substantially pure 1-propynyl-3-methyl-3-phospholene-1-oxide free from the 1-allenyl isomer.

EXAMPLE 8

Conversion of 1-chloro-3-methyl-3-phospholene to a mixture of the 2- and 3-isomers of 1,3-dimethylphospholene-1-oxide without isolation of intermediates To a solution of 131.9 g. (0.98 mole) of 1-chloro-3-methyl-3-phospholene in 400 ml. of 1,2-dichloroethane maintained at 5° to 10° C with stirring, there was added a total of 72.05 g. (1.25 mole) of propylene oxide over a period of 10 minutes. The resulting mixture was stirred for 30 minutes at the same temperature and then 94.08 g. (3 mole) of anhydrous methanol was added. The mixture was stirred for 15 minutes and then 10.68 g. (0.1 mole) of ethyl bromide was added. The mixture so obtained was stirred for 2 hours at room temperature before adding a second portion of 10.68 g. of ethyl bromide and heating the mixture under reflux for 2.5 hours. The solvent was evaporated from the reaction product and the residue was distilled in vacuo to obtain 116.4 g. (91.3% theoretical yield) of a mixture of the 2- and 3-isomers (containing 63.6% of the 2-isomer) of 1,3-dimethylpholene-1-oxide.

EXAMPLE 9

Preparation of 1-allyl-3-methyl-3-phospholene-1-oxide.

To 8 g. (0.0448 mole) of 1-(chloropropoxy)-3-methyl-3-phospholene there was added 2.9 g. (0.05 mole) of allyl alcohol. The mixture was allowed to stand at room temperature and then distilled under reduced pressure to remove volatile material. There was thus obtained 1-allyl-3-methyl-3-phospholene-1-oxide.

EXAMPLE 10

Preparation of 1-(1-hydroxymethylprop-3-enyl)-3methyl-3-phospholene-1-oxide.

A total of 8.1 g. (0.045 mole) of 1-(chloropropoxy)-3-methyl-3-phospholene was added rapidly with stirring to 8.8 g. (0.1 mole) of 2-butene-1,4-diol. The resulting cloudy mixture was heated at 125° C for a short period (2 minutes) and then was subjected to distillation in vacuo to obtain 1-(1-hydroxymethylprop-3-enyl)-3-methyl-3-phospholene-1-oxide in the form of a liquid.

EXAMPLE 11

Preparation of 1-(1-hydroxymethylallenyl)-3-methyl-3-phospholene-1-oxide.

A total of 14.3 g. (0.08 mole) of 1-(chloropropoxy)-3-methyl-3-phospholene was added in two halves to a suspension of 6.8 g. (0.08 mole) of 2-butyn-1,4-diol in 25 ml. of 1,2-dichloroethane. The second half of the phospholene was added dropwise after the slow exotherm, generated by the first addition, had subsided. The maximum temperature reached in the first exotherm was 45° C and, in the second exotherm, was 60° C. After the addition of all phospholene was complete, the mixture was stirred for 30 minutes without heating and then was heated under reflux for 30 minutes. At the end of this time the solvent was removed by distillation and the residue was distilled in vacuo. There was thus obtained 1-(1-hydroxymethylallenyl)-3-methyl-3-phospholene-1-oxide in the form of a liquid.

EXAMPLE 12

Preparation of 1-butyl-3-methyl-3phospholene-1-oxide.

To a solution of 26.4 g. (0.137 mole) of 1-(chloropropoxy)-3-methyl-3-phospholene in 57 ml. of 1,2-dichlorobutane was added 30.4 g. (0.411 mole) of n-butanol. The mixture was heated under reflux for 4 hours and then the solvent was removed by evaporation. The residue was distilled under reduced pressure to obtain 15.4 g. (65.3% yield) of 1-butyl-3-methyl-3-phospholene-1-oxide in the form of a liquid having a boiling point of 106° – 116° C at 0.2 mm. of mercury.

EXAMPLE 13

Preparation of 1-isobutyl-3-methyl-3-phospholene-1-oxide.

Using the procedure described in Example 12 but replacing the n-butanol by the same amount of isobutyl alcohol and increasing the time of reflux to 12.5 hours, there was obtained 7.1 g. (29.4% yield) of 1-isobutyl-3-methyl-3-phospholene-1-oxide in the form of a liquid having a boiling point of 85° to 92° C at 0.3 mm. of mercury.

EXAMPLE 14

Preparation of 1-isopropyl-3-methyl-3-phospholene-1-oxide.

To a solution of 8.5 g. (0.0442 mole) of 1-(chloropropoxy)-3-methylphospholene in 18.5 ml. of 1,2-dichloroethane was added 5.3 g. (0.088 mole) of anhydrous isopropyl alcohol. The resulting mixture was heated under reflux for 9 hours at the end of which time the solvent was stripped and the residue was distilled under reduced pressure. There was thus obtained 1-isopropyl-3-methyl-3-phospholene-1-oxide in the form of a liquid having a boiling point of 84° to 88° C at 0.2 mm. of mercury.

We claim:

1. A process for the preparation of a phospholene-1-chalcogenide having an aliphatic hydrocarbyl substituent attached to the phosphorus atom, having a double bond in the 2-or 3- position, and having the carbon atoms in the ring of said phospholene free of substituents other than inert substituents, and wherein the chalcogen is selected from the group consisting of oxygen and sulfur, which process comprises reacting the corresponding 1-(2-chloroalkoxy)-3-phospholene with at least one equivalent, per mole of the latter phospholene, of a member selected from the group consisting of aliphatic alcohols and aliphatic thiols at a temperature within the range of about −20° to about 160° C.

2. A process which comprises the step of reacting (a) a phospholene having the formula:

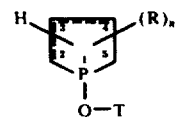

wherein the broken line indicates a double bond located between the carbon atom at position 3 and one of the carbon atoms at positions 2 and 4, the H atom is attached to whichever carbon atom at positions 2 and 4 is not part of said double bond, R is a substituent selected from the group consisting of halogen, alkoxy from 1 to 6 carbon atoms, inclusive, phenoxy, hydrocarbyl from 1 to 6 carbon atoms, inclusive, and halohydrocarbyl from 1 to 6 carbon atoms, inclusive, $n$ is a whole number from 0 to 3, and T is 2-chloroalkoxy from 2 to 6 carbon atoms with (b) at least one equivalent per mole of said phospholene, of a member selected from the group consisting of monohydric and polyhydric aliphatic alcohols and monohydric and polyhydric thiols; at a temperature in the range of about −20° to 160° C to obtain a corresponding phospholene-1-chalcogenide having the formula:

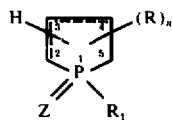

wherein R and n have the significance hereinbefore defined, Z is selected from the group consisting of oxygen and sulfur, and $R_1$ is the aliphatic residue of said member (b).

3. A process which comprises the step of reacting (a) a phospholene of the formula:

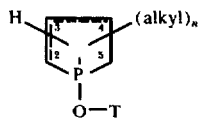

wherein the broken line indicates a double bond located between the carbon atom at position 3 and one of the carbon atoms at positions 2 and 4, the H atom is attached to whichever carbon atom at positions 2 and 4 is not part of said double bond, n is a whole number from 0 to 3 and T is 2-chloroalkoxy from 2 to 6 carbon atoms with (b) at least one equivalent per mole of said phospholene, of a lower aliphatic alcohol $R_2OH$ wherein $R_2$ is selected from the class consisting of lower-alkyl, lower-alkenyl and lower-alkynyl; at a temperature in the range of −20° to 160° C to obtain the corresponding phospholene oxide having the formula:

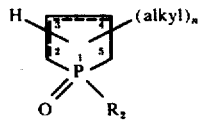

wherein n and $R_2$ are as above defined.

4. A process which comprises the step of reacting 1-(2-chloropropoxy)-3-methyl-3-phospholene with at least one equivalent, per mole of said phospholene, of a lower aliphatic alcohol at a temperature in the range of about 50° to about 140° C to obtain a mixture of 1-lower-alkyl-3-methyl-2-phospholene-1-oxide and 1-lower-alkyl-3-methyl-3-phospholene-1-oxide.

5. The process of claim 4 wherein the reaction is carried out in the presence of a catalytic amount of an alkyl halide.

6. The process of claim 5 wherein the alkyl halide is ethyl bromide.

7. The process of claim 4 wherein the 1-(2-chloropropoxy)-3-methyl-3-phospholene employed as starting material is obtained by reaction of 1-chloro-3-methyl-3-phospholene with propylene oxide and the reaction product so obtained is reacted, without purification, with the lower-aliphatic alcohol.

8. The process of claim 4 wherein the lower aliphatic alcohol is methanol and the product is a mixture of 1,3-dimethyl-3-phospholene-1-oxide and 1,3-dimethyl-2-phospholene-1-oxide.

9. The process of claim 4 wherein the lower aliphatic alcohol is ethanol and the product is a mixture of 1-ethyl-3-methyl-3-phospholene-1-oxide and 1-ethyl-3-methyl-2-phospholene-1-oxide.

10. The process of claim 4 wherein the lower aliphatic alcohol is butanol and the product is a mixture of 1-butyl-3-methyl-3-phospholene-1-oxide and 1-butyl-3-methyl-2-phospholene-1-oxide.

11. The process of claim 4 wherein the lower aliphatic alcohol is isopropyl alcohol and the product is a mixture of 1-isopropyl-3-methyl-3-phospholene-1-oxide and 1-isopropyl-3-methyl-2-phospholene-1-oxide.

12. A process for the preparation of a mixture of 1,3-dimethyl-3-phospholene-1-oxide and 1,3-dimethyl-2-phospholene-1-oxide which comprises reacting 1-(chloroethoxy)-3-methyl phospholene with at least one equivalent per mole of said phospholene, of methanol in the presence of a catalytic amount of ethyl bromide.

13. A process for the preparation of a mixture of 1,3-dimethyl-3-phospholene-1-oxide and 1,3-dimethyl-2-phospholene-1-oxide which comprises reacting 1-(chloropropoxy)-3-methylphospholene with at least one equivalent per mole of said phospholene, of methanol in the presence of a catalytic amount of ethyl bromide.

* * * * *